United States Patent [19]
Soezima

[11] Patent Number: 4,962,516
[45] Date of Patent: Oct. 9, 1990

[54] METHOD AND APPARATUS FOR STATE ANALYSIS

[75] Inventor: Hiroyoshi Soezima, Kyoto, Japan

[73] Assignee: Shimadzu Corporation, Kyoto, Japan

[21] Appl. No.: 302,148

[22] Filed: Jan. 27, 1989

Related U.S. Application Data

[63] Continuation of Ser. No. 747,423, Jun. 21, 1985, abandoned.

[51] Int. Cl.$^5$ ............................................. G01N 23/223
[52] U.S. Cl. ........................................ 378/45; 378/49; 250/307; 250/310
[58] Field of Search .................... 378/45, 46, 49, 82, 378/83; 250/306, 307, 310

[56] References Cited

U.S. PATENT DOCUMENTS

| | | | |
|---|---|---|---|
| 2,897,367 | 7/1959 | Andermann et al. | 378/83 |
| 3,103,584 | 9/1963 | Shapiro et al. | 250/307 |
| 4,476,386 | 10/1984 | Reid et al. | 250/307 |
| 4,559,450 | 12/1985 | Robinson et al. | 250/310 |

OTHER PUBLICATIONS

Compton, A. H., *X-Rays and Electrons*, D. van Nostrand Co., New York, 1926, pp. 54–57.
Baun, W. L., "Characterization of Thin Anodized Films on Aluminum with Soft X-Ray Spectroscopy", Jour. Electrochem. Soc. (USA), vol. 123, No. 1, Jan. 1976.

*Primary Examiner*—Craig E. Church
*Attorney, Agent, or Firm*—Birch, Stewart, Kolasch & Birch

[57] ABSTRACT

A method for analyzing a state of an element in a specimen comprises the steps of applying an exciting source to the element, detecting the intensity of characteristic X-rays generated from measurement points at two wavelengths previously selected depending on the state of the element to be analyzed, comparing the intensity ratio of the characteristic X-rays at the two wavelengths to detect some measurement points providing the detected intensity ratio falling within a range selected depending on the state of the element, and outputting state detection signals detected only at said some measurement points to obtain a line analysis or a two-dimensional scanning image.

13 Claims, 3 Drawing Sheets

METHOD AND APPARATUS FOR STATE ANALYSIS

This application is a continuation, of application Ser. No. 747,423 filed on June 21, 1985 now abandoned.

FIELD OF THE INVENTION

The present invention relates to method and apparatus for state analysis and, more particularly, to method and apparatus for state analysis directed to a line analysis or a two-dimensional scanning image based on elemental state data, such as the chemical bonding state, of elements contained in specimens.

An Electron Probe Micro Analyzer (EPMA) or so is operated to apply electron beam or X-rays as exciting source to the specimens, so that the intensity of characteristic X-rays emitted from the specimens is measured to obtain the elemental data.

DESCRIPTION OF THE PRIOR ART

Conventionally, the EPMA for analyzing the surface state of a specimen is so operated that it irradiates electron beam to the surface of the specimen and detects characteristic X-rays from micro area of about 1 μm to obtain elemental analysis data of the specimen.

Basically, the EPMA is designed and constructed so as to analyze elements, but not to directly analyze any compound. Therefore, even if a specimen contains Fe metal, FeO, $Fe_3O_4$, and $Fe_2O_3$, all of them are detected and equally treated in terms of Fe elemental spectra in the EPMA. However, the spectrum of the characteristic X-rays detected by the EPMA can be changed by the state (mainly, chemical bonding state) of the respective elements in the specimen. Therefore, it may be possible to carry out the state analysis by detecting the change of the spectrum of the characteristic X-rays. Unfortunately, the degree of the spectra change of the characteristic X-rays is normally too small to collect data necessary for the state analysis even when the spectrometer is set in a specific wavelength of the characteristic X-ray with scanning the electron beams.

In view of this, the so-called "point analysis" is carried out wherein the spectrometer is operated to respond to a plurality of wavelengths emanating from a point in connection with an element to be analyzed so as to obtain peak profiles and analyze the wavelength spectra.

Normally, a two-dimensional scanning image in only some specific chemical bonding state cannot be obtained except for some peculiar cases such as in sulfides and sulfuric acids, or CuO and $Cu_2O$. The reason is that in the peculiar cases, different inherent peak can appear, being separated depending on the chemical bonding state in L-emission band spectra of sulfur, or Oxygen K-emission band spectra of copper oxides. In these cases, when the spectrometer is set in either inherent peak wavelength, the two-dimensional state distribution image can be given. Such a method, however, is not applicable to the normal cases because the peaks inherent to the element state can rarely appear in the ordinal wavelength of the EPMA (about 1 through 100 Å).

It may be possible in principle that a great number of point analyses are carried out in connection with the respective measurement points of the specimen to analyze their spectra, automatically with a computer. However, in the case of line analysis and the two-dimensional scanning image, the measurement points are about several hundreds to several tens of thousands, so that the operation time and the memory capacity become vast.

SUMMARY OF THE INVENTION

Accordingly, it is an object of the present invention to provide improved method and apparatus for performing a state analysis of elements.

It is another object of the present invention to provide improved method and apparatus for carrying out a line analysis or obtaining a two-dimensional scanning image in substantially real time.

It is a further object of the present invention to provide an improved apparatus being capable of carrying out a line analysis or a two-dimensional scanning image with apparatus of a simple construction.

Other objects and further scope of applicability of the present invention will become apparent from the detailed description given hereinafter. It should be understood, however, that the detailed description and specific examples, while indicating preferred embodiments of the invention, are given by way of illustration only, since various changes and modifications within the spirit and scope of the invention will become apparent to those skilled in the art from this detailed description.

To achieve the above objects, pursuant to embodiment of the present invention, a state analysis method is characterized in that the intensity or energy level (amplitude) of characteristic X-rays emitted from one or more measurement points of a specimen is detected for two different predetermined spectral wavelengths previously selected by a spectrometer depending on a specific state of an element to be analyzed. The intensity or amplitude values in a single spectrum (the number of photons) in respect to different energy positions is obtained. If the intensity ratio i.e. the ratio of the amplitude values of the respective X-ray energies detected at the two selected wavelengths falls within a predetermined range selected according to the specific state of the element in some measurement points, state detection signals detected only at those measurement points are outputted to display a line analysis or a two-dimensional scanning image. According to the state analysis method of the present invention, the spectral intensity ratio detected with the two different wavelengths selected is used to detect the change of the spectrum in order to determine the state.

A state analysis apparatus of the present invention comprises two wavelength dispersive spectrometers and a comparator. The two wavelength dispersive spectrometers are set to different wavelengths of characteristic X-rays to meet with specific state of the element to be analyzed. The comparator is operated to compare the intensity or energy level (amplitude) of the characteristic X-rays detected at the two wavelengths by the spectrometers with each other and determines whether the intensity ratio of the amplitude values falls within a predetermined range. Only when the intensity ratio falls within the range, the comparator outputs state detection signals.

Further, according to the present invention, one wavelength dispersive spectrometer comprises a wavelength dispersion crystal and a position sensitive detector (PSD) for detecting characteristic X-rays dispersed by the wavelength dispersion crystal. The characteristic X-rays are detected at different positions previously defined by the PSD. A comparator is provided for comparing the intensity of the characteristic X-rays detected at the two positions of PSD with each other. Only if the intensity ratio is within a predetermined range selected depending on the specific state of the element, the comparator outputs state detection signals.

BRIEF DESCRIPTION OF THE DRAWINGS

The present invention will become more fully understood from the detailed description given hereinbelow and the accompanying drawings which are given by way of illustration only, and thus are not limitative of the present invention and wherein.

DESCRIPTION OF THE PREFERRED EMBODIMENTS

FIGS. 1 through 4 are graphs of spectra of characteristic X-rays are helpful in explaining a method of the present invention.

Figure 1:
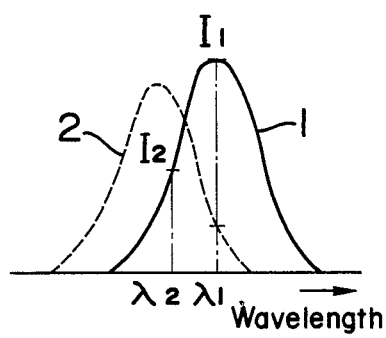
FIGS. 1 through 4 are graphs of spectra of characteristic X-rays used for explaining a method of the present invention.

FIG. 1 shows spectra of characteristic X-ray of elements Si or $SiO_2$, for example, contained in the specimen. The changing from Si to $SiO_2$ enables the shift of the peak wavelength in the spectrum of the characteristic X-rays. When the element of Si is in a first state i.e. metallic Si, it provides spectrum 1 of FIG. 1 as the inherent characteristic X-rays. In the spectrum 1, the peak wavelength value is $\lambda_1$. A wavelength value far from $\lambda_1$, at about a half of half width (at most at the peak half width) is $\lambda_2$. Since the values of $\lambda_1$ and $\lambda_2$ are previously known depending on an element to be analyzed, two spectrometers are set to the wavelengths $\lambda_1$ and $\lambda_2$, respectively. When the two spectrometers detect the spectrum, the intensity detected is given to be $I_1$ and $I_2$. It is assumed that they satisfy the following relation.

$$I_1 \geq \alpha\beta_1 I_2 \qquad (1)$$

$\alpha$ is an inherent factor so that the sensitivity of a first spectrometer for measuring the intensity $I_1$ at the wavelength $\lambda_1$ becomes equal to that of a second spectrometer for measuring the intensity $I_2$ at the wavelength $\lambda_2$. The factor $\alpha$ is defined according to the spectrometers. $\beta_1$ is a factor representative of the wavelength shift amount in the characteristic X-ray spectra, the factor being defined with corresponding to the specific state of the element to be analyzed.

In a second state of the Si element, it is the compound of, for example, $SiO_2$. The spectra of the Si element in this second state is shifted toward the shorter wavelengths due to the effect of oxygen to be spectrum 2 and displaced from spectrum 1. The peak wavelength value of the spectra 2 is thereby shifted toward the shorter wavelengths.

When the two spectrometers set to the wavelengths $\lambda_1$ and $\lambda_2$ are used to detect the spectral characteristic X-rays in the second state, the intensity $I_1$ and $I_2$ satisfy the following relation.

$$I_1 < \alpha\beta_1 I_2 \qquad (2)$$

Therefore, the characteristic X-rays of the element to be analyzed are detected based on the wavelengths $\lambda_1$ and $\lambda_2$ previously selected in order to compare the detected intensity data with each other. To detect the first state of the element $S_1$, state detection signals are outputted in connection with only some measurement points providing the intensity ratio for satisfying the relation (1), so that a line analysis or a two-dimensional scanning image in the first state can be displayed. To detect the second state of the combination of Si with O, namely $SiO_2$, state detection signals are outputted from only some measurement points providing the intensity ratio for satisfying the inequality (2), so that the line analysis or the two-dimensional scanning image in the second state also be displayed.

Figure 2:
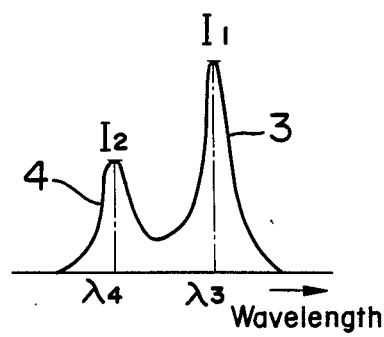

FIG. 2 shows a graph of spectra of the characteristic X-rays where the intensity ratio of the related peaks are changed depending on the specific state such as the chemical bonding, for example, in the case of $L\alpha$ and $L\beta$ of Fe or $\alpha_3$ and $\alpha_4$ of K satellites.

Two spectrometers are set to peak wavelengths $\lambda_3$ and $\lambda_4$ of the two related peaks 3 and 4. In the first state, the detected intensity data $I_1$ and $I_2$ of the characteristic X-rays at the selected wavelengths $\lambda_3$ and $\lambda_4$ are assumed to satisfy the following relation.

$$I_1 \geq \alpha\beta_2 I_2 \qquad (3)$$

In the second state, the intensity data $I_1$ and $I_2$ are assumed to satisfy the following relation.

$$I_1 < \alpha\beta_2 I_2 \qquad (4)$$

$\beta_2$ is a factor representative of the intensity ratio of the related peaks. The line analysis or the two-dimensional scanning image specific to the states can be given by determining whether the spectra of the characteristic X-rays at the measurement points belong to either of the relations (3) and (4).

Figure 3:
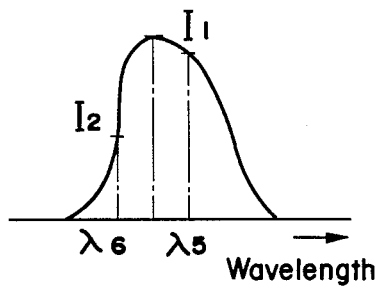

FIG. 3 shows a graph of the spectrum of the characteristic X-rays wherein symmetry in the spectrum is changed depending on the change of the state such as the chemical bonding states. The two spectrometers are set to wavelengths $\lambda_5$ and $\lambda_6$, respectively, which are, for example, about a half of the half width, at the longer and shorter wavelength sides. Determined is whether the intensity data of the characteristic X-rays at the selected wavelengths $\lambda_5$ and $\lambda_6$ satisfy one of the following relations.

$$I_1 > \alpha\beta_3 I_2 \qquad (5)$$

$$I_1 = \alpha\beta_3 I_2 \qquad (6)$$

$$I_1 < \alpha\beta_3 I_2 \qquad (7)$$

$\beta_3$ is a factor representative of asymmetry in the spectrum of the characteristic X-rays. By detecting one of the relations, the line analysis or the two-dimensional scanning image specific to the state to which the spectra belong can be obtained.

Figure 4:
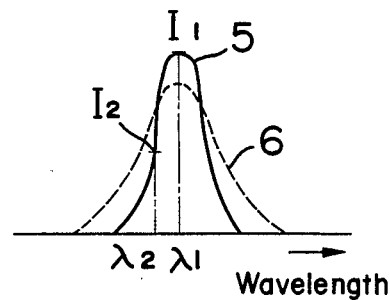

FIG. 4 shows a graph of spectrum of the characteristic X-rays where the half width in the spectrum of the characteristic X-rays can be altered depending on the changes of the state such as the chemical bonding state. When it is assumed that the spectrum is altered as shown in spectra 5 and 6 depending on the changes of the state, the wavelengths of the two spectrometers should be selected to be $\lambda_1$ of the peak wavelength and $\lambda_2$ far from $\lambda_1$ at about a half of the half width as shown in FIG. 1. The line analysis or the two-dimensional scanning image can be given in the same method as in FIG. 1 because the detected intensity ratio can be changed at the selected wavelength if the peak half width of the spectra is changed.

Figure 5:
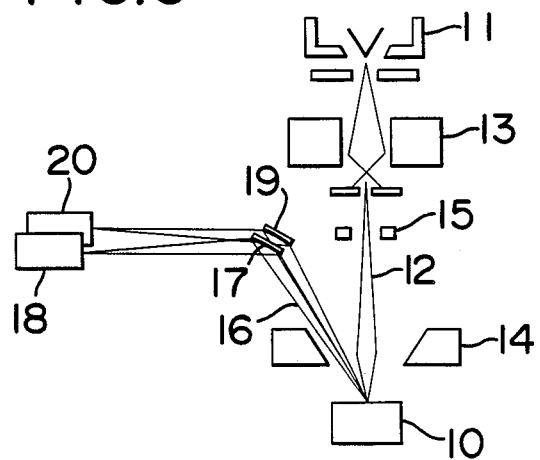
FIG. 5 is a schematic arrangement of a state analysis apparatus according to a first preferred embodiment of the present invention.

FIG. 5 is a schematic representation of a state analysis apparatus according to a first preferred embodiment of the present invention.

An electron beam 12 emitted from an electron gun 11 is incident upon a measurement point on a sample 10 to be analyzed with a focusing lens 13 and an objective lens 14. A scanning coil 15 is provided for enabling the scanning on the sample 10. In response to the application of the electron beam 12, a characteristic X-ray 16 and secondary electrons are emitted from the sample 10.

In the first preferred embodiment of the present invention, a first and second wavelength dispersive spectrometers are provided to detect the characteristic X-rays 16. The first wavelength dispersive spectrometer comprises a spectroscopic crystal 17 as a wavelength dispersion means and a detector 18. The second wavelength dispersive spectrometer comprises a spectroscopic crystal 19 as a wavelength dispersion means and a detector 20. The two spectrometers with the same sensitivity can detect the characteristic X-rays having the wavelengths specified in FIGS. 1 through 4; i.e., one of them is set to $\lambda_1$, $\lambda_3$, or $\lambda_5$, while another to $\lambda_2$, $\lambda_4$, or $\lambda_6$, respectively.

The detectors 18 and 20 may be a proportional counter, position sensitive detector, etc. It is preferable that both spectrometers are positioned adjacently to each other to make a measurement condition similar.

Figure 6:
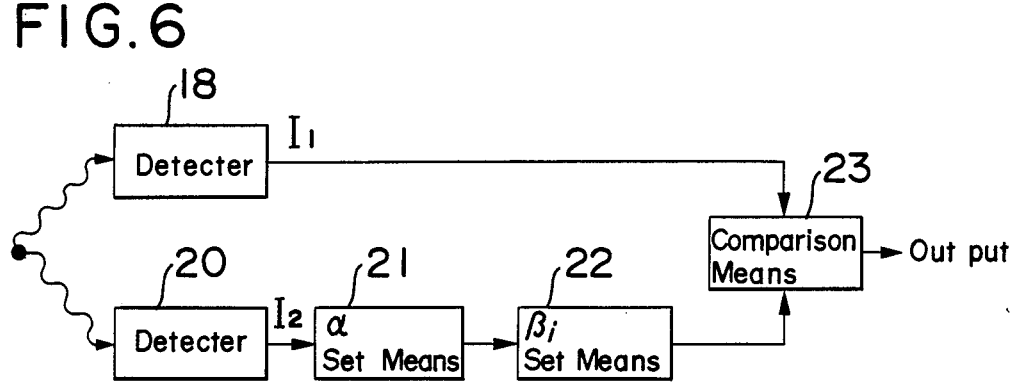
FIGS. 6 through 8 are block diagrams of the state analysis apparatus of FIG. 5 to process state detection signals.

The characteristic X-rays 16 emitted from the sample 10 are dispersed to different wavelengths with the spectroscopic crystals 17 and 19 and are detected by the detectors 18 and 20 at the same time or sequentially. It is assumed that the detected spectral intensity of the two detectors 18 and 20 is $I_1$ and $I_2$, respectively. The intensity value $I_2$ is changed to "$\alpha\beta I_2$" with an $\alpha$ set means 21 and a $\beta i$ ($i=1, 2,$ or 3) set means 22 as FIG. 6 shows. A comparison means 23 is provided for comparing $I_1$ with $\alpha\beta i I_2$ so as to determine whether any specific state is specified. While a plurality of measurement points are scanned with displaying the state detection in real time on a display, a line analysis or a two-dimensional scanning image can be displayed.

Figure 7:
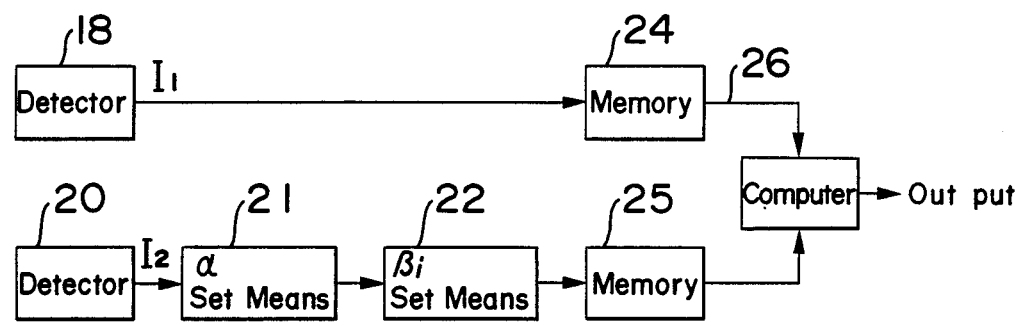
Figure 8:
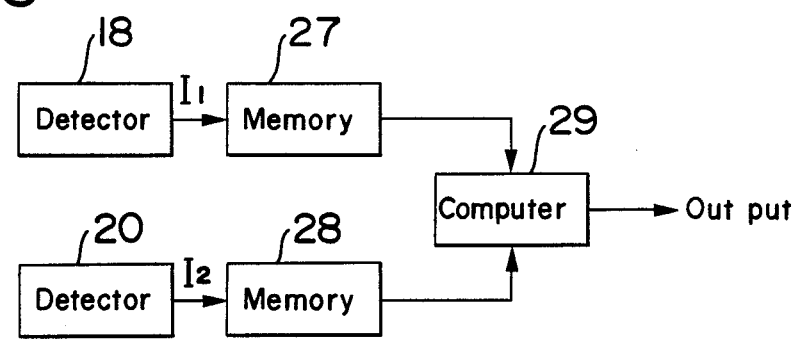

As FIG. 7 shows, the output signals from the detectors 18 and 20 are stored in memories 24 and 25 in the form of the data $I_1$ and $\alpha\beta i I_2$, respectively, together with the position information of the measurement point. Thereafter, a computer 26 is operated to compare the data with each other. Otherwise, as FIG. 8 shows, the intensity data $I_1$ and $I_2$ from the detectors 18 and 20 are directly stored in memories 27 and 28 together with the position information of the measurement point. Thereafter, a computer 29 is operated to add the two coefficients $\alpha$ and $\beta i$ and compare the resultant data with each other so as to display the result.

Figure 9:
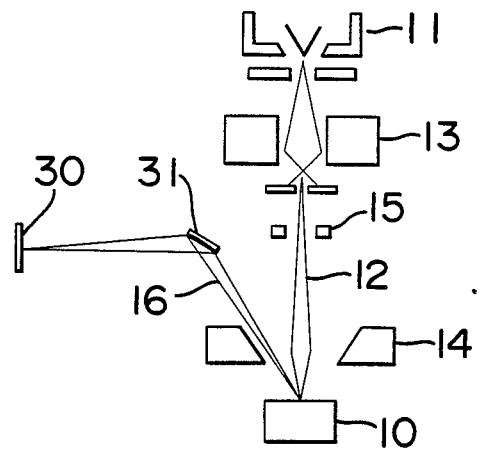
FIG. 9 is a schematic arrangement of a state analysis apparatus according to a second preferred embodiment of the present invention.

FIG. 9 is a schematic illustration of a state analysis apparatus according to a second preferred embodiment of the present invention. The state analysis apparatus of FIG. 9 is different from that of FIG. 5 in that a single wavelength dispersive spectrometer is provided which comprises a position sensitive detector 30 and a spectroscopic crystal 31 and that the intensity data by the position sensitive detector 30 are detected at two positions, respectively, corresponding to one selected wavelength ($\lambda_1$ for example) and another selected wavelength ($\lambda_2$ for example).

In case where the two independent spectrometers are provided for measuring the intensity data at the two selected wavelengths $\lambda_1$ and $\lambda_2$, each of them can be placed in a completely spectroscopic condition. On the other hand, in case where only the single spectrometer with the position sensitive detector is provided for simultaneously measuring the intensity data at the positions corresponding to the wavelengths $\lambda_1$ and $\lambda_2$, a spectroscopic condition is approximated. This is, however, no problem in practice to compare the intensity data between the adjacent wavelengths.

Figure 10:
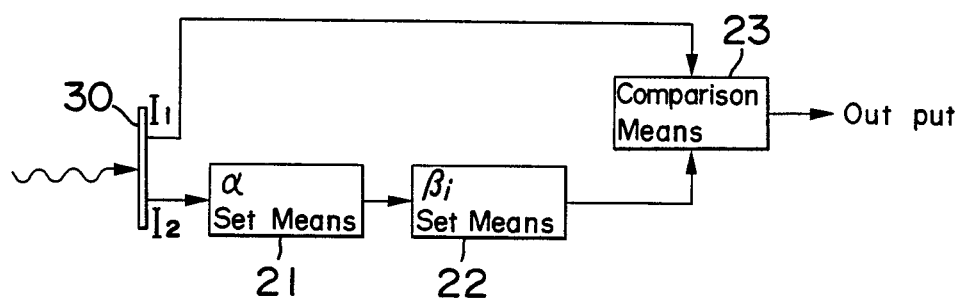
FIG. 10 is a block diagram of the state analysis apparatus of FIG. 9 to process state detection signals.

In the second preferred embodiment, as FIG. 10 shows, two portions of the single position sensitive detector 30 provide the intensity data $I_1$ and $I_2$ in the two different selected wavelengths, simultaneously or sequentially. In FIG. 10, the intensity data $I_1$ and $I_2$ are processed in real time. Otherwise they are processed after being stored within the memories 24, 25, 27, and 28 as shown in FIGS. 7 and 8. A line analysis or a two-dimensional scanning image at the specific state can be thereby displayed.

As described above, in accordance with the present invention, in case where the state of an element contained in a specimen is altered depending on the chemical bonding state, the characteristic X-ray spectra are correspondingly altered in a condition in which a point analysis mode can be applied to analyze the spectra. In such a case, the characteristic X-ray spectra can be effectively separated and altered. A line analysis or a two-dimensional scanning image of a composition distribution in the specimen to be analyzed can be displayed, having the same real time as the conventional case. The capability of the EPMA can be highly expanded beyond the conventional capability only for analyzing the element, in that according to the present invention, the EPMA can afford the important information of the state analysis in analyzing a material.

The invention being thus described, it will be obvious that the same may be varied in many ways. Such variations are not to be regarded as a departure from the spirit and scope of the invention, and all such modifications are intended to be included within the scope of the following claims.

What is claimed is:

1. A method for analyzing the chemical bonding state of an element in a specimen, comprising the steps of:
   applying a beam of X-rays or electrons from a source to at least one measurement point of the specimen including said element;
   detecting signals of the intensity of the characteristic X-rays generated and emitted from said measurement point at two selected different wavelengths within the spectrum of the characteristic X-rays generated by said element in a first bonding state, said wavelengths being selected to provide a change in intensity ratio for different chemical bonding states of the element being analyzed as compared to the intensity ratio of the element in the first bonding state;
   multiplying one of the respective signals of energy intensity by a factor related to a change in spectral shape of characteristic X-ray spectrum detected for said element in the respective bonding states in order to obtain a product;

comparing the product with the other of said detected signals of intensity at said measurement point and determining the ratio thereof; and generating output signals corresponding to a chemical bonding state when the product to intensity ratio falls within a predetermined range of ratio values which is indicative of a known chemical bonding state.

2. The method according to claim 1 wherein said two wavelengths comprise a first wavelength and a second wavelength, said first wavelength being longer than said second wavelength.

3. The method according to claim 1 wherein said step of applying comprises applying said beam to a plurality of measurement points.

4. The method according to claim 1 wherein said other detected signal comprises the signal of said second wavelength.

5. The method according to claim 4 wherein said factor representative of change in spectral shape is related to a change in the amount of wavelength shift in the characteristic X-ray spectrum.

6. The method according to claim 4 wherein said factor representative of change in spectral shape is related to a change in the intensity ratio of related peaks in the characteristic X-ray spectrum.

7. The method according to claim 4 wherein said factor representative of change in spectral shape is related to a change in symmetry of the characteristic ray spectrum.

8. Apparatus for analyzing the chemical bonding state of an element in a specimen by detecting a spectral change of X-rays emitted from the specimen in response to application of a beam of X-rays or electrons to the specimen comprising:

means for applying a beam of X-rays or electrons to the specimen;

means for detecting signals of the intensity of energy amplitude levels of the characteristic X-rays generated and emitted from a measurement point at two selected different wavelengths within the spectrum of the characteristic X-rays generated by said element in the first bonding state, said wavelengths being selected to provide a change in intensity ratio for different chemical bonding states of the element being analyzed as compared to the intensity ratio of the element in the first bonding state;

multiplying one of the respective signals of energy intensity by a factor related to a change in spectral shape of characteristic X-ray spectrum detected for said element in the respective bonding states in order to obtain a product;

means for comparing the product with the other of said detected signals of intensity at said measurement point and determining the intensity ratio thereof; and means for generating output signals corresponding to a chemical bonding state when the product to intensity ratio falls within a predetermined range of ratio values which is indicative of a known chemical bonding state.

9. The apparatus according to claim 8 and additionally including means for applying said beam to a plurality of measurement points.

10. The apparatus according to claim 8 wherein said one detected signal comprises the signal of said second wavelength.

11. The apparatus according to claim 10 wherein said factor representative of change in spectral shape is related to the amount of wavelength shift in the characteristic X-ray spectrum between bonding states.

12. The apparatus according to claim 10 wherein said factor representative of change in spectral shape is related to a change in the intensity ratio of related peaks in the characteristic X-ray spectrum.

13. The apparatus according to claim 10 wherein said factor representative of change in spectral shape is related to a change in the symmetry of the characteristic ray spectrum.

* * * * *